(12) United States Patent
Hartley et al.

(10) Patent No.: US 9,060,895 B2
(45) Date of Patent: *Jun. 23, 2015

(54) ROTATIONAL CONTROLLED DEPLOYMENT DEVICE

(75) Inventors: David Ernest Hartley, Wannanup (AU); Werner Dieter Ducke, Greenwood (AU)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 649 days.

This patent is subject to a terminal disclaimer.

(21) Appl. No.: 13/502,940

(22) PCT Filed: Oct. 14, 2010

(86) PCT No.: PCT/US2010/052635
§ 371 (c)(1),
(2), (4) Date: May 15, 2012

(87) PCT Pub. No.: WO2011/049808
PCT Pub. Date: Apr. 28, 2011

(65) Prior Publication Data
US 2012/0221091 A1    Aug. 30, 2012

Related U.S. Application Data

(60) Provisional application No. 61/279,399, filed on Oct. 20, 2009.

(51) Int. Cl.
*A61F 2/06* (2013.01)
*A61F 2/966* (2013.01)
*A61F 2/95* (2013.01)

(52) U.S. Cl.
CPC . *A61F 2/966* (2013.01); *A61F 2/95* (2013.01); *A61F 2002/9517* (2013.01); *A61F 2002/9665* (2013.01)

(58) Field of Classification Search
CPC .......... A61F 2/2436; A61F 2/966; A61F 2/95; A61F 2/962; A61F 2/2427
USPC ............... 606/108; 623/1.11, 1.12, 1.23, 2.11
See application file for complete search history.

(56) References Cited

U.S. PATENT DOCUMENTS

| 2007/0255390 A1 | 11/2007 | Ducke et al. |
| 2008/0262590 A1 | 10/2008 | Murray |
| 2011/0282425 A1* | 11/2011 | Dwork ........................ 623/1.11 |

FOREIGN PATENT DOCUMENTS

| EP | 1518516 | 3/2005 |
| WO | WO2009/023221 | 2/2009 |

OTHER PUBLICATIONS

International Search Report and Written Opinion for PCT/US2010/052635 dated Feb. 24, 2011, 12 pgs.
Examination Report for EP 10 774 047.4 dated Mar. 17, 2015, 4 pgs.

* cited by examiner

*Primary Examiner* — Jonathan W Miles
(74) *Attorney, Agent, or Firm* — Brinks Gilson & Lione

(57) ABSTRACT

A stent graft deployment device assembly (10) has a cylindrical fixed handle (6) to be gripped and held by a user and an tubular release handle (30) extending through the fixed handle. The release handle can be moved through the fixed handle. The deployment device assembly has a pusher assembly and a sheath (18) to cover a stent graft on the pusher assembly. The pusher assembly is connected to the fixed handle and the sheath is connected to the release handle so that retraction of the release handle through the fixed handle causes the sheath to be retracted from the stent graft on the pusher assembly. The fixed handle has a rotator component (36) with internal first and second screw threads. The tubular release handle has an external screw thread (31) which engages with the first screw thread. The external screw thread (31) can extend along part, all or in segments along the release handle. A release clamp (48) on the pusher has pins which engage with the second screw thread. Movement of the rotator component with respect to the fixed handle first moves the tubular release handle with respect to the fixed handle and subsequently moves the release clamp on the pusher and thereby pulls the trigger wires.

20 Claims, 12 Drawing Sheets

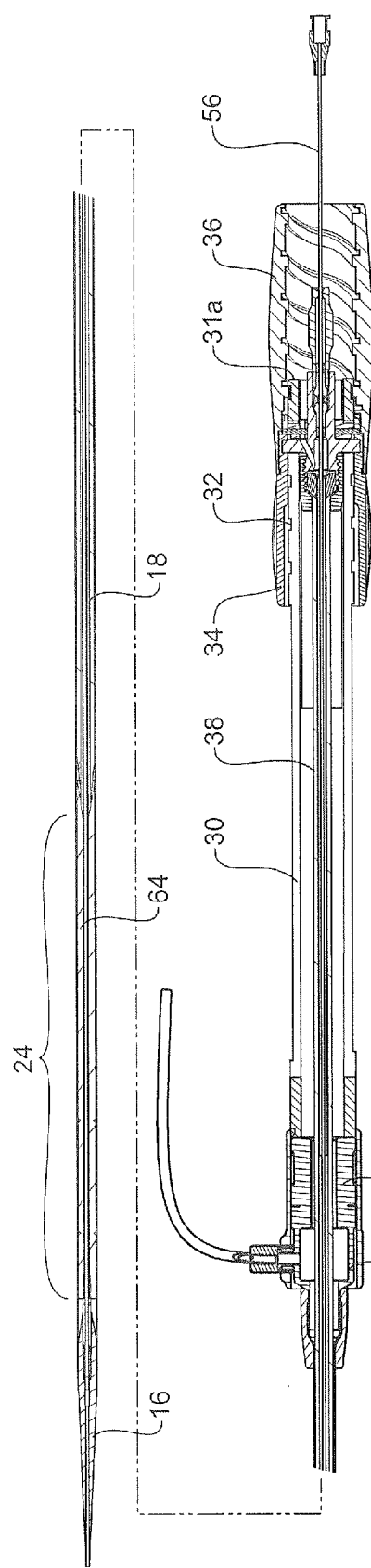
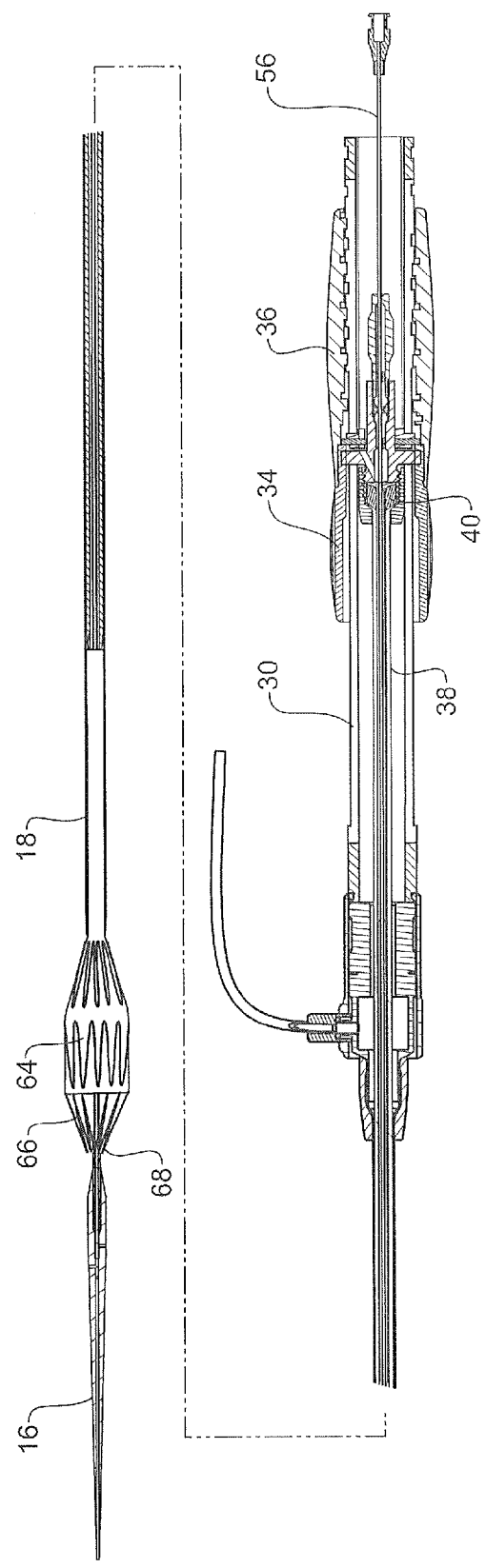
Fig 4A
Fig 4B

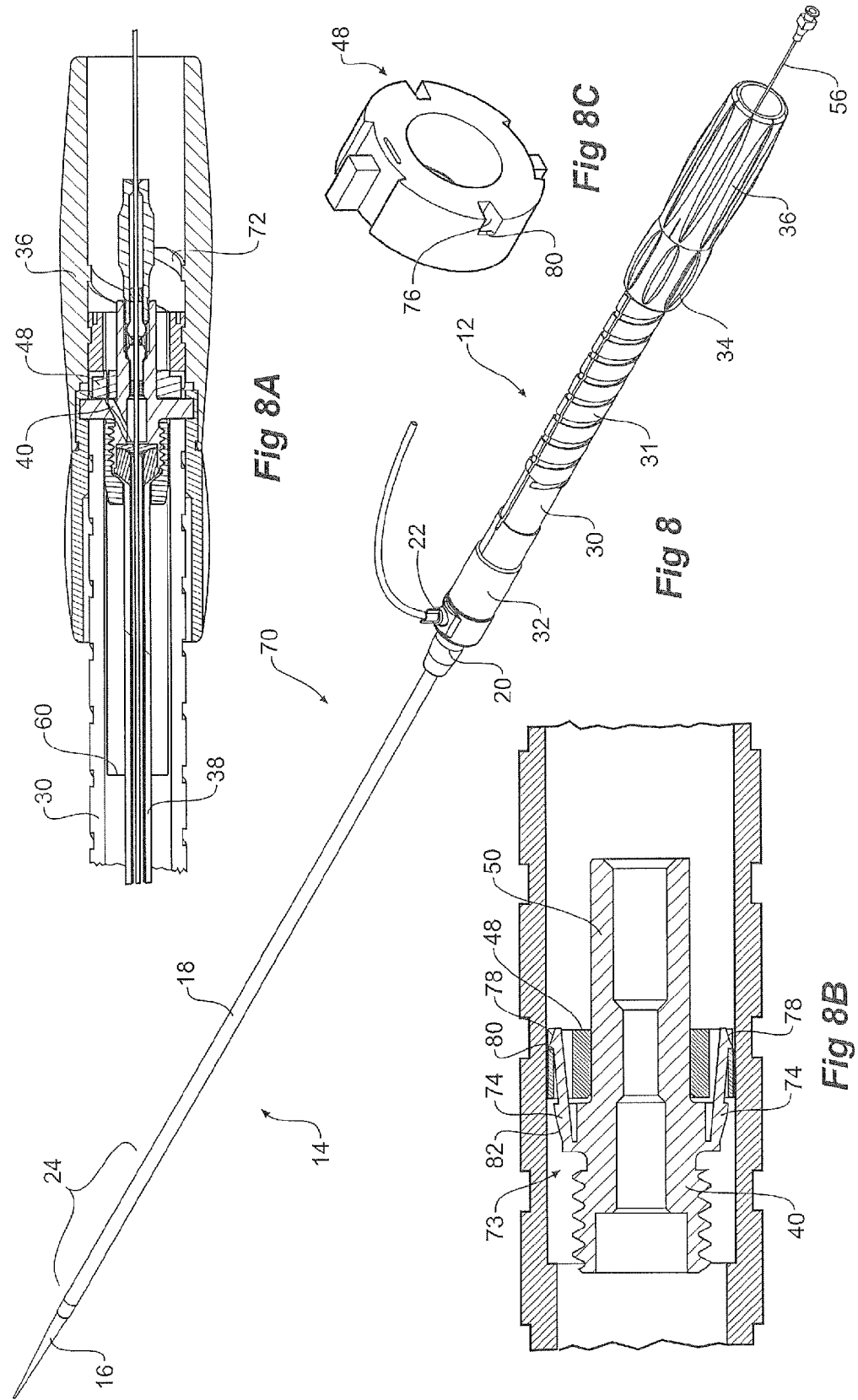

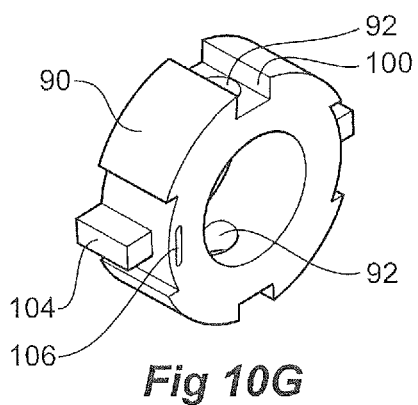
Fig 10G
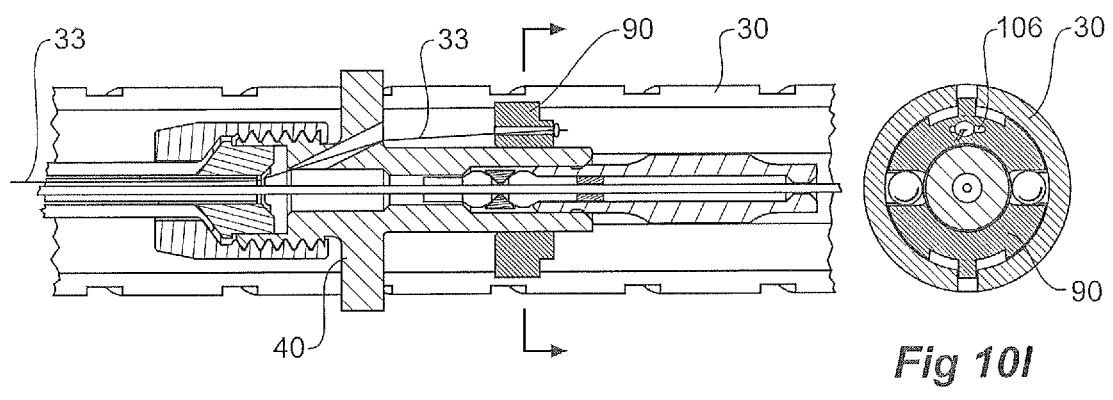
Fig 10H
Fig 10I

ROTATIONAL CONTROLLED DEPLOYMENT DEVICE

RELATED APPLICATIONS

The present patent document is a §371 filing based on PCT Application Serial No. PCT/US2010/052635, filed Oct. 14, 2010 (and published as WO 2011/049808 A1 on Apr. 28, 2011), designating the United States and published in English, which claims the benefit of the filing date under 35 U.S.C. §119(e) of Provisional U.S. Patent Application Ser. No. 61/279,399, filed Oct. 20, 2009. All of the foregoing applications are hereby incorporated by reference in their entirety.

INCORPORATION BY REFERENCE

The following co-pending patent application is referred to in the following description:
PCT Publication WO 2003/101518 entitled "Trigger Wire System for a Prosthesis Deployment Device"
The entire contents of this application is hereby incorporated herein by reference.

TECHNICAL FIELD

This invention relates to a medical device and more particularly to a device for endovascular deployment of a stent graft and even more particularly to an actuation handle for such a device.

BACKGROUND ART

An introducer for a stent graft is a device which retains a stent graft in a contracted condition so that it can be deployed by endovascular techniques and then releases the stent graft when it is properly positioned within the vasculature of a patient.

It is desirable that a set of sequential actions necessary to release the stent graft from an introducer at a desired position in the vasculature be undertaken in the required order and that there be less chance for operator error during such a deployment.

It is the object of this invention therefore to provide a deployment device which is arranged to introduce, deploy and release a stent graft by a series of sequential actions.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

The invention will in general be discussed in relation to deployment of a stent graft into the abdominal aorta but the invention is not so limited and can apply to deployment into other portions of the aorta or into other vessels of the human or animal body.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the invention.

Disclosure of The Invention

In one form therefore, the invention is said to reside in an endovascular introducer comprising in combination, a handle assembly, a stent graft deployment device and a stent graft retained on the stent graft deployment device, the handle assembly including a first part and a second part, the second part to be moved relative to the first part, the first part comprising a fixed portion to be gripped and held by a user and rotating portion to be rotated, the rotating portion of the first part and the second part comprising co-acting first screw threads whereby rotation of the second part with respect to the rotating portion of the first part causes relative longitudinal motion between the first part and the second part, the deployment device including a pusher assembly, the stent graft being mounted onto the pusher assembly and a sheath to cover the stent graft on the pusher assembly and to retain the stent graft in a compressed condition on the pusher assembly, the sheath being relatively movable with respect to the pusher assembly, the pusher assembly being connected to the first part and the sheath being connected to the second part whereby retraction of the second part with respect to the first part by the relative rotation thereof causes the sheath to be retracted at least partially from the stent graft on the pusher assembly.

Preferably the fixed portion of the first part engages the pusher and the rotating portion of the first part engages a release clamp on the pusher, the release clamp being movable longitudinally with respect to the pusher, the release clamp on the pusher having attached thereto trigger wires for the release of the stent graft from the pusher assembly, whereby movement of the second component with respect to the first component moves the release clamp on the pusher and thereby pulls the trigger wires to release the stent graft from the pusher assembly.

Preferably the rotating portion of the first part rotates with respect to the fixed portion of the first part and the rotating portion includes a second screw thread with a portion of the release clamp engaged into the second screw thread whereby rotational movement of the second part causes longitudinal movement of the release clamp with respect to the pusher assembly.

Preferably the rotating portion comprises an internal cylindrical surface and both the first screw thread and the second screw thread are formed on the internal cylindrical surface, the first screw thread and the second screw thread comprising the same pitch and being concentric with each other.

Preferably the first screw thread comprises a 3 mm by 1 mm helical protrusion with a 32 mm pitch on the internal cylindrical surface of the second component and the second screw thread comprises a 2 mm by 2 mm helical groove with a 32 mm pitch on the internal cylindrical surface of the second component.

The co-acting first screw thread on the second part can extend part of the length of the second part or substantially the full length of the second part.

Preferably the first screw thread comprises a 3 mm by 1 mm helical protrusion with a 32 mm pitch on the internal cylindrical surface of the second component and the second screw thread comprises a 2 mm by 2 mm helical groove with a 32 mm pitch on the internal cylindrical surface of the second component.

Preferably the device further includes a stepped shoulder on the second part, the stepped shoulder arranged to engage the release clamp on the pusher assembly after a selected amount of longitudinal movement of the second part has occurred by the relative rotation of the first part to thereby cause the portion of the release clamp to engage into the second screw thread to thereby start to pull the trigger wires to release the stent graft from the pusher assembly.

Preferably the second part includes a bayonet socket for a hub of the sheath whereby the sheath and sheath hub move with the second part and the sheath can be disengaged from the bayonet socket if required.

Preferably the first part is substantially cylindrical and the second part is tubular and slides within the first part.

Preferably the tubular second part has longitudinal slots and an internal lumen and the pusher assembly extends within the longitudinal lumen and the pusher assembly includes arms which extend through the longitudinal slots to engage with the first part whereby the second part can be moved longitudinally with respect to the first part.

In an alternative embodiment the invention comprises a stent graft deployment device assembly, the device including a cylindrical fixed handle to be gripped and held by a user and an tubular release handle extending through the fixed handle whereby the release handle can be moved through the fixed handle, the deployment device assembly further including a pusher assembly and a sheath to cover a stent graft on the pusher assembly, the pusher assembly being connected to the fixed handle and the sheath being connected to the release handle whereby retraction of the release handle through the fixed handle causes the sheath to be retracted from the stent graft on the pusher assembly, the fixed handle including a grip component which grips the pusher assembly and a rotator component, the rotator component comprising a first screw thread and a second screw thread on an internal cylindrical surface thereof, the first screw thread and the second screw thread comprising the same pitch and being concentric, the tubular release handle comprising an external screw thread engageable with the first screw thread, a release clamp on the pusher assembly, the release clamp on the pusher assembly having trigger wires for the release of the stent graft from the pusher assembly attached thereto, the release clamp comprising pins engaging with the second screw thread whereby movement of the rotator component with respect to the grip component first moves the tubular release handle with respect to the grip component and subsequently moves the release clamp on the pusher assembly and thereby pulls the trigger wires.

The external screw thread on the tubular release handle can extend part of the length of the tubular release handle from a distal end thereof or can extend substantially the full length of the tubular release handle from a distal end thereof. Where the external screw thread on the tubular release handle extends part of the length of the tubular release handle from a distal end thereof the retraction of the sheath by rotation of the rotator component occurs until the external screw thread disengages from the first screw thread at which time further retraction of the sheath can be achieved by longitudinal movement of the release handle through the fixed handle. Where the external screw thread on the tubular release handle extends substantially the full length of the tubular release handle complete the retraction of the sheath by rotation of the rotator component can occur.

Preferably the first screw thread comprises a 3 mm by 1 mm helical protrusion with a 32 mm pitch on the internal cylindrical surface of the rotator component and the second screw thread comprises a 2 mm by 2 mm helical groove with a 32 mm pitch on the internal cylindrical surface of the rotator component and the external screw thread engageable with the first screw thread comprises a 3 mm by 1 mm helical groove with a 32 mm pitch.

Preferably the release handle includes a bayonet socket for a hub of the sheath.

Preferably the fixed handle comprises a substantially cylindrical bore therethrough and the release handle is tubular and slides within the fixed handle.

Preferably the tubular release handle has longitudinal slots therealong and an internal lumen and the pusher assembly extends within the longitudinal lumen and the pusher assembly includes arms which extend through the longitudinal slots to engage with the fixed handle whereby the release handle can be moved with respect to the fixed handle to move the sheath with respect to the pusher assembly.

The device can further include a stepped shoulder on the release handle, the stepped shoulder arranged to engage the release clamp on the pusher assembly after a selected amount of movement of the release handle has occurred by the relative rotation of the rotator to thereby pull the trigger wires to release of the stent graft from the pusher assembly. Preferably the stepped shoulder is inside the release handle It will be seen that by the various forms of this invention, a device is provided which by the action of holding one portion of the deployment device and moving another portion of the deployment device in a rotational motion, the various sequential actions necessary to release the stent graft can occur in a selected order.

BRIEF DESCRIPTION OF THE DRAWINGS

This then generally describes the invention but to assist with understanding, reference will now be made to the accompanying drawings which show preferred embodiments of the invention.

In the drawings:

FIGS. 4A and 4B show a detailed longitudinal cross sectional views of the embodiment of FIG. 1;

FIG. 8 shows a perspective view of an alternative embodiment of a deployment device according to the present invention;

FIGS. 8A and 8B show detailed longitudinal cross sections of parts of the embodiment shown in FIG. 8;

FIG. 8C shows a perspective view of the release clamp of the embodiment shown in FIG. 8;

FIGS. 10A to 10I show various stages of the action of an alternative release clamp retention system.

DESCRIPTION OF PREFERRED EMBODIMENTS

Figure 1:
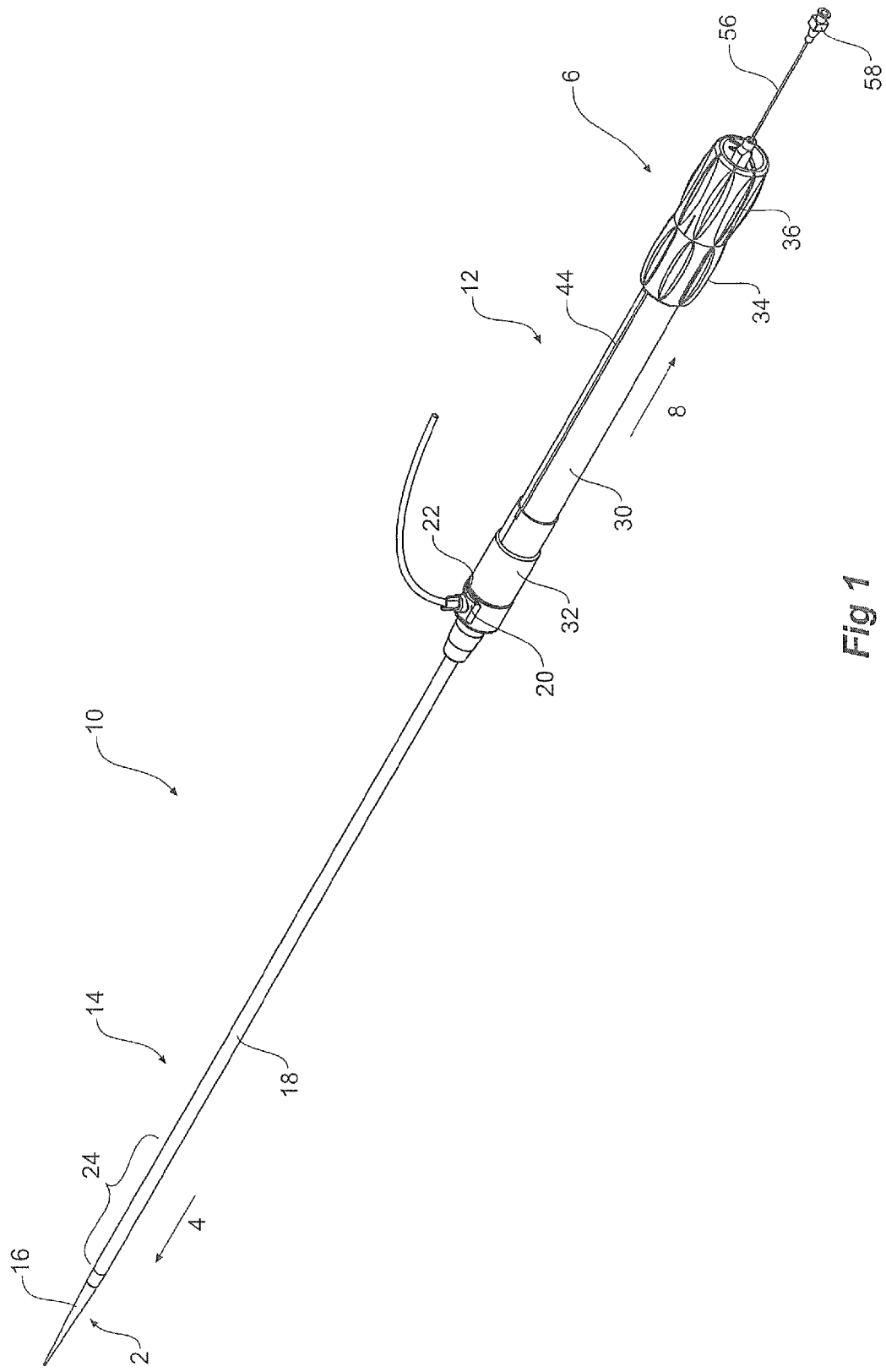
FIG. 1 shows a perspective view of an embodiment of a deployment device according to the present invention.
Figure 6:
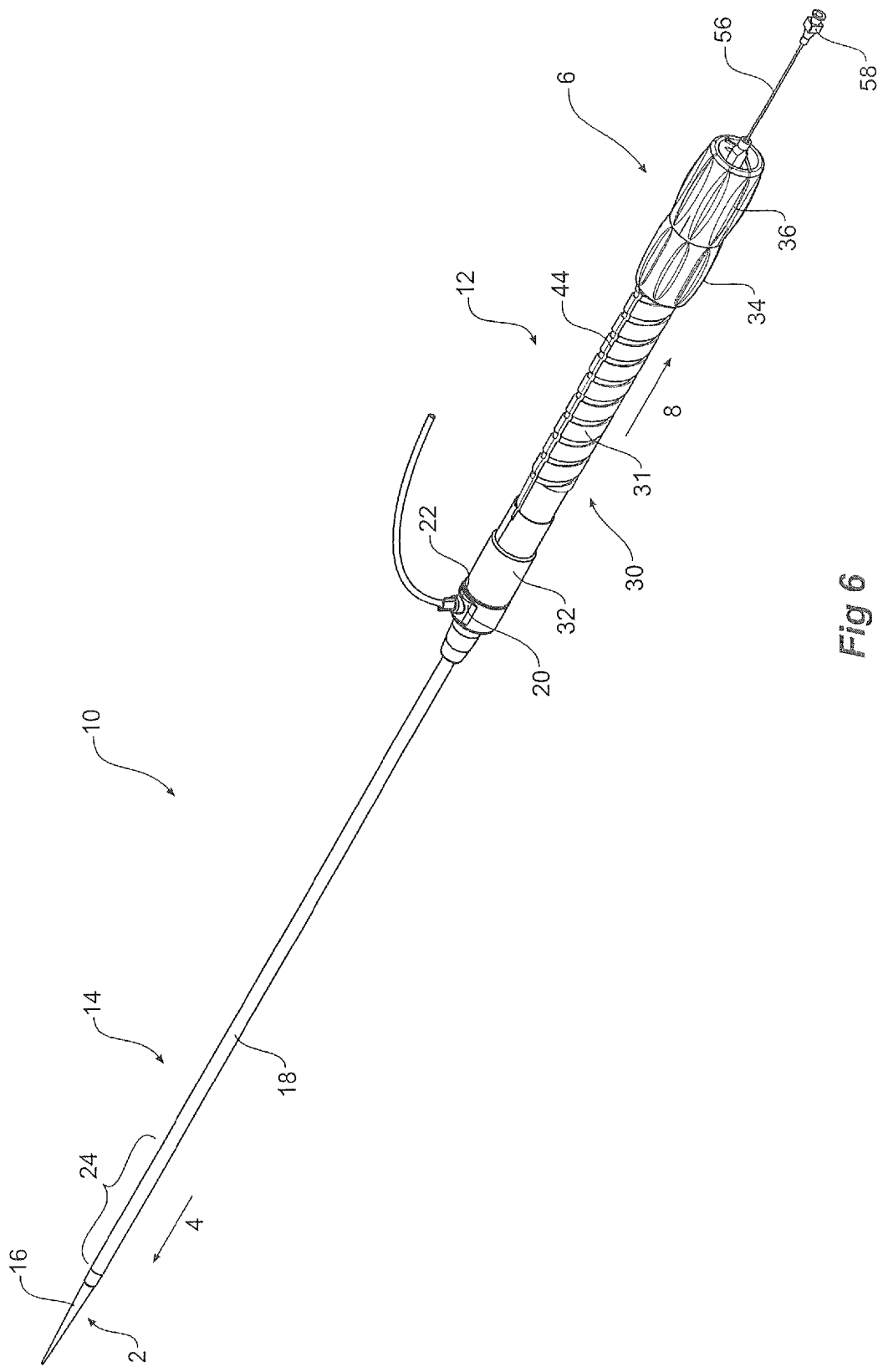
FIG. 6 shows a perspective view of an alternative embodiment of a deployment device according to the present invention.

Throughout this discussion and as shown in FIGS. 1 and 6 the term proximal means the end 2 of the handle and stent graft deployment device assembly 10 and the direction proximally means in the direction shown by the arrow 4. The term distal means the end 6 of the handle and stent graft deployment device assembly 10 and the direction distally means in the direction shown by the arrow 8.

Now looking more closely at the FIGS. 1 to 5 of the drawings it will be seen that the handle and stent graft deployment device assembly 10 of this embodiment includes a handle portion 12 and a stent graft delivery portion 14. The delivery portion 14 is arranged to be deployed within the vasculature of a patient by the Seldinger technique to deliver and release a stent graft within the vasculature and the handle portion 12 remains outside the patient to be manipulated by a physician to deliver and release the stent graft.

The delivery portion 14 includes a nose cone dilator 16 and a sheath 18 extending from a sheath hub 20 which is engaged into the handle portion 12 with a bayonet type fitting 22. A stent graft is retained underneath the sheath 18 in the region 24 immediately distal of the nose cone dilator 16. The device is introduced into a patient over a guide wire (not shown) which passes through the guide wire catheter 56. The sheath hub 20 has haemostatic seals 20a (see FIG. 4A) through which passes the pusher 38 of the delivery device.

The handle assembly 12 comprises a release handle 30 which includes a proximal grip 32 and a fixed handle 34 to which is attached a rotator component 36. The fixed handle 34 is substantially cylindrical with a grip pattern on its outer surface. The fixed handle 34 is composed of fixed handle halves 34a and 34b which together fit around the release handle 30. The rotator component 36 is also substantially cylindrical with a grip pattern on its outer surface.

Figure 5A:
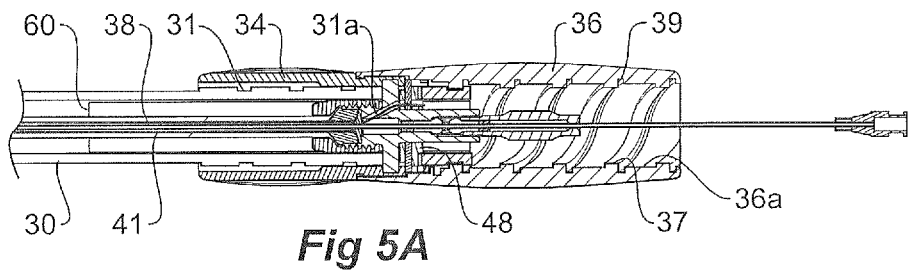
FIGS. 5A to 5E shows a detailed longitudinal cross sectional view of the fixed and rotating handle portion of the embodiment of FIG. 1 at various stages of deployment.

As can be best seen in FIG. 5A the rotator component 36 is substantially cylindrical with a grip pattern on its outer surface. The rotator component 36 includes first and second screw threads on its internal cylindrical surface 36a. The first screw thread 37 comprises a protrusion from the internal surface 36a. In one embodiment the first screw thread 37 has a pitch of 32 mm and comprises a protrusion with a depth of 1 mm and a width of 3 mm. The second screw thread 39 is formed as a cut or groove in the internal surface 36a. In one embodiment the screw thread 39 has a pitch of 32 mm and comprises a helical groove with a depth of 2 mm and a width of 2 mm. Hence the first and second screw threads 37 and 39 comprise the same pitch and are concentric.

Figure 2:
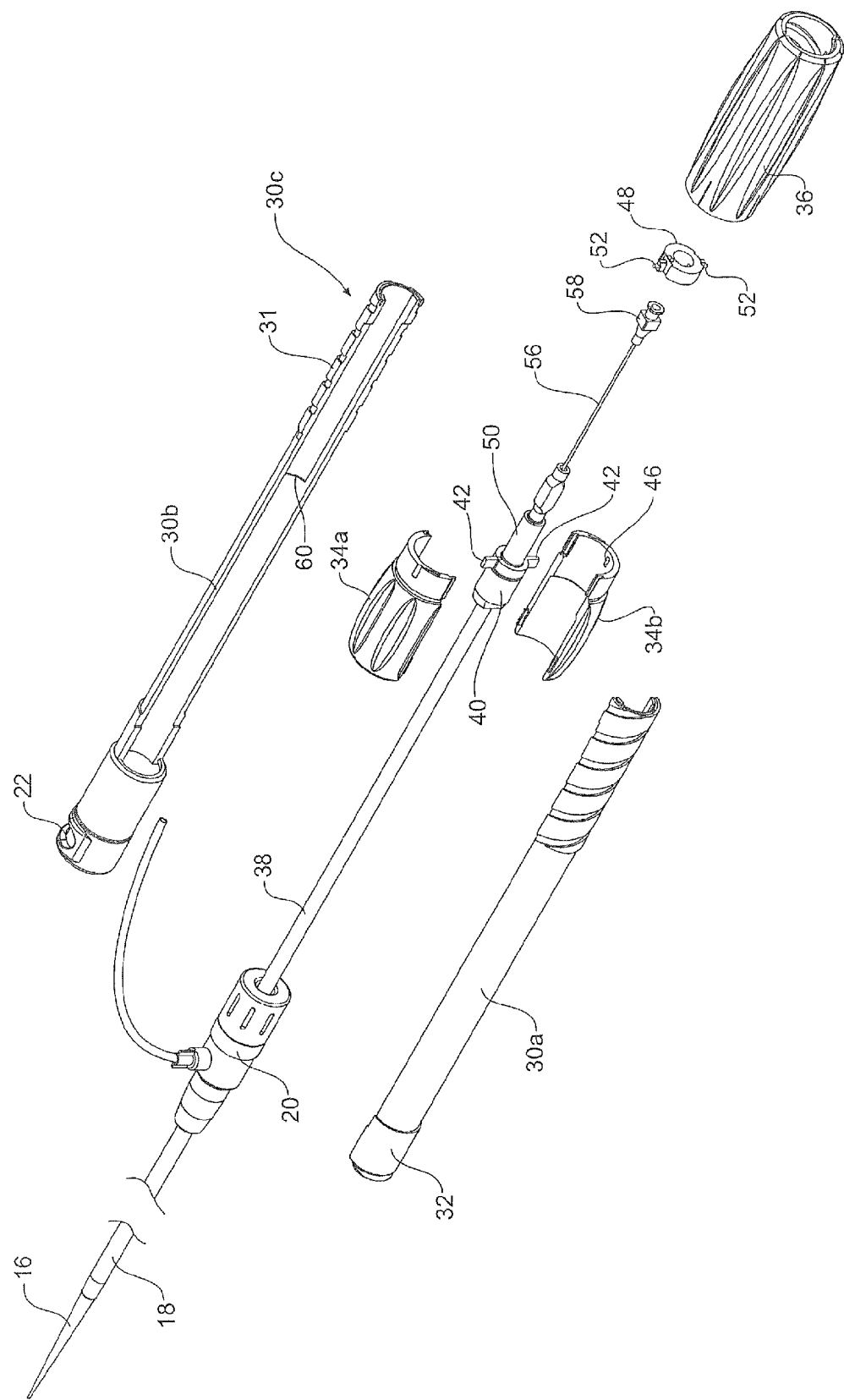
FIG. 2 shows an exploded view of the handle portion of the device shown in FIG. 1.

As can be seen in detail in FIG. 2 the release handle 30 is formed from semi-cylindrical release handle halves 30a and 30b which fit together around a pusher 38 for the stent graft delivery device. The release handle 30 has formed on its outer surface towards its distal end 30c a screw thread 31. The screw thread 31 on the outer surface of the release handle 30 engages with the first screw thread 37 on the internal surface 36a of the rotator component 36. Hence, in one embodiment the screw thread 31 has a pitch of 32 mm and comprises a groove with a depth of 1 mm and a width of 3 mm.

The pusher 38 includes a pusher hub 40 which includes pins 42 extending diametrically in each direction from the hub 40 and which pins 42 extend through a slot 44, as best can be seen in FIG. 1, which extends longitudinally along the release handle 30 and engage into apertures 46 in the fixed handle halves 34a and 34b. The pusher hub 40 also includes a release clamp 48 which slides along a cylindrical portion 50 of the hub 40. The release clamp 48 includes pins 52 which extend diametrically through the slot 44 in the release handle 30 and engage into the second screw thread 39 within the rotator component 36. The second screw thread 39 can best be seen in FIG. 5A.

Release or trigger wires 33 (see FIGS. 5D and 5E) extend from each end of the stent graft 64 (see FIG. 4) retained in the delivery device in the region 24. The release or trigger wires 33 pass through a lumen 41 in the pusher 38 and a haemostatic seal within the pusher hub 40 and are fixed to the release clamp 48. The function of the release wires is discussed in more detail in relation to FIGS. 5A to 5E.

The delivery device includes the guide wire catheter 56 and a syringe hub 58 at the distal end of the guide wire catheter 56. The guide wire catheter 56 extends through the pusher hub 40 and the lumen 41 within the pusher 38 to and through the nose cone dilator 16. The stent graft 64 is retained concentrically around the guide wire catheter 56 immediately distal of the nose cone dilator 16.

The release handles are each substantially semi-cylindrical and when joined together form a tubular body and include inside and positioned at a selected position along their length is a stepped shoulder 60. The stepped shoulder 60 is used to determine when the release of the trigger or release wires for the stent graft is to be activated as will be discussed in relation to FIGS. 5A to 5E.

Figure 3:
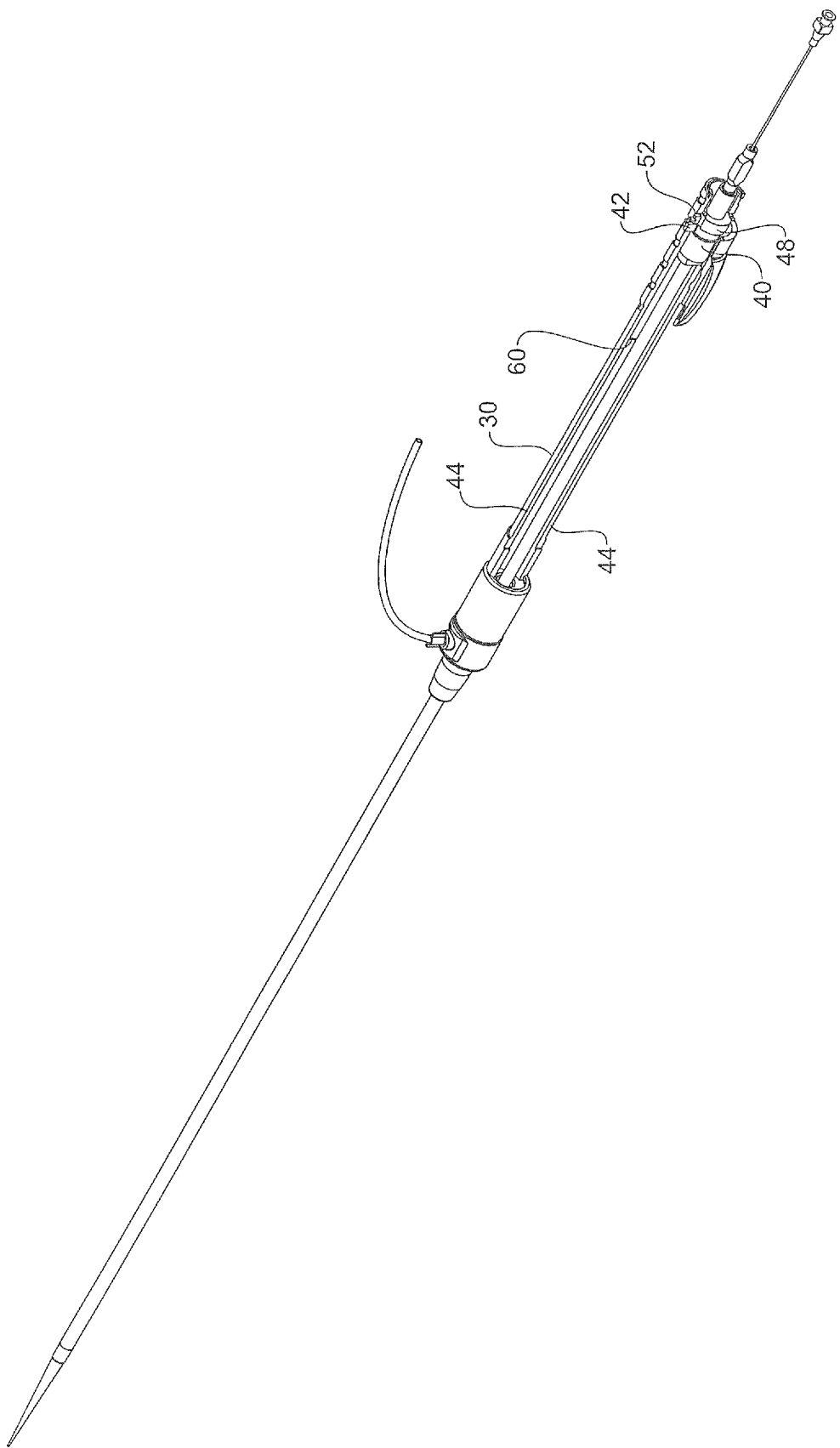
FIG. 3 shows an assembled and part cut away view of the handle portion of the device shown in FIG. 1.

FIG. 3 shows a cut-away assembled view of the handle portion of the delivery device. It can be particularly seen that the slot 44 in the release handle 30 is on both sides of the release handle and the position of the stepped shoulder 60. This means that there needs to be a certain amount of travel of the release handle through the fixed handle and rotator component before the stepped shoulder 60 engages the release clamp. The rotator component 36 has been omitted from FIG. 3 so that the pusher hub 40 and pins 42 on the pusher hub 40 and the pins 52 on the release clamp 48 can be easily seen.

FIGS. 4A and 4B shows a longitudinal cross-sectional view of the device of the embodiment of the invention shown in FIG. 1 showing the device before delivery and at a stage in the operation of the device respectively.

In FIG. 4A the distal end 31a of the screw thread 31 on the release handle 30 is just engaging the first screw thread 37 on the internal cylindrical surface 36a of the rotator component 36.

At the stage shown in FIG. 4B the fixed handle 34 and rotator component 36 have been gripped and release handle 30 has been moved through the fixed handle 34 by rotation of the rotator component 36 which moves the screw thread 31 on the release handle 30 along the first screw thread 37 on the internal cylindrical surface 36a of the rotator component. The pusher 38 and pusher hub 40 have been held essentially steady because they are engaged using pins 42 (FIG. 3) into the fixed handle 34 but drawing back the release handle 30 has caused the sheath 18 to move distally back from the nose cone dilator 16 which has allowed the stent graft 64 to be partially exposed. At this stage an exposed stent 66 at the proximal end of the stent graft 64 is still engaged to a release arrangement at the distal end 68 of the nose cone dilator 16 and approximately two covered stents of the stent graft are exposed. The position of the shoulder 60 sets the amount of retraction before the shoulder 60 engages against the release clamp 48 as will be discussed below. Also at this stage the release handle has not been engaged by the shoulder so the pins 52 extending from the release handle are not yet engaged into the second screw thread 39 on the internal cylindrical surface 36a of the rotator component 36.

A method of retention of the proximal end of a stent graft onto an introducer is disclosed in PCT Publication WO2003/101518 entitled "Trigger Wire System for a Prosthesis Deployment Device". This feature and other features disclosed in PCT Publication WO2003/101518 could be used with the present invention and the disclosure of PCT Publication WO2003/101518 is herewith incorporated in its entirety into this specification.

FIGS. 5A to 5E show the various stages in deployment of a stent graft using the deployment assembly of the present invention. In each of these drawings detail is shown of the fixed handle and rotator component of the handle portion of the assembly.

In FIG. 5A the release handle is at its initial position in the fixed handle and rotator component of the handle portion of the assembly At this stage the stent graft 64 (see FIG. 4A) is held in a contracted state by the sheath 18 which extends back to the sheath hub 20. The stent graft is also retained at least at its proximal end to the delivery device by release or trigger wires (not shown) which extend back to the release clamp 48 through the lumen 39 of the pusher 38 and pusher hub 40 and then through the duct 41 a in the pusher hub 40 and fastened to the release clamp 48. There can also be a similar release or trigger wire system for retention and release of the distal end of the stent graft and trigger wires for this extend back to the release clamp 48 through the lumen 39 of the pusher 38 and pusher hub 40 and then through the duct 41 in the pusher hub 40 and also fastened to the release clamp 48.

Movement of the release clamp 48 with respect to the pusher hub 40, as discussed below, will retract the trigger wires from engagement with the stent graft 64 thereby releasing the stent graft. It is desirable that the proximal end of the stent graft 64 is released after at least two stents of the stent graft have been exposed and allowed to expand and hence the second screw thread 39 on the rotator component 36 is arranged to engage the pins 52 on the release clamp 48 only after the stepped shoulder 60 has engaged against the release clamp 48 to move the pins on the release clamp into engagement with the second screw thread. It is desirable, also that the trigger wire retaining the distal end 64b of the stent graft 64, if present, is only released after the stent graft is fully exposed as is shown in FIG. 9 below. To achieve this the trigger wire is made significantly longer to extend well beyond its engagement with the stent graft at the distal end of the stent graft. This means that as the release clamp 48 continues being retracted after it has been released from the rotator component 36 and moved distally by its engagement with the stepped shoulder 60 and the trigger wire for the distal end 64b of the stent graft is not released from its engagement until the sheath 18 has been fully retracted from the stent graft 64.

Both the fixed handle 34 and rotator component 36 are dimensioned so that the cylindrical body of the release handle 30 can pass through them as it is moved distally and the pusher hub 40 and the release clamp 48 are dimensioned so that the cylindrical body of the release handle 30 can pass around them. The stepped shoulder 60 and the release clamp 48 are dimensioned so that while the stepped shoulder will pass around the pusher hub 40 it engages against the release clamp 48.

Figure 5B:
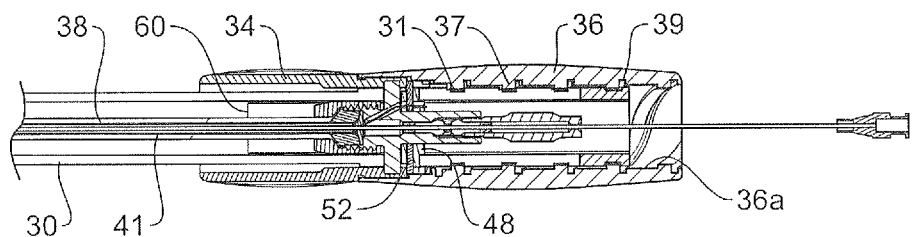

Partial retraction of the release handle 30 is shown in FIG. 5B. This is achieved by rotation of the rotator component 36 with respect to the fixed handle 34 so that the screw thread 31 and hence the release handle 30 engaged with first screw thread 37 of the rotator component 36 and hence is driven through the rotator component. At this stage the pusher hub 40 and the release clamp 48 are retained in their positions relative to the fixed handle 34 and rotator component 36 by the pins 42 and 52 respectively engaging into them. The proximally extending exposed stent 66 on the stent graft 64 is exposed by retraction of the sheath 18 and the very proximal end of the stent graft has also been exposed but not to a stage where the proximal end of the stent graft can start to expand under the action of its self expanding stents (see FIG. 4B).

Figure 5C:
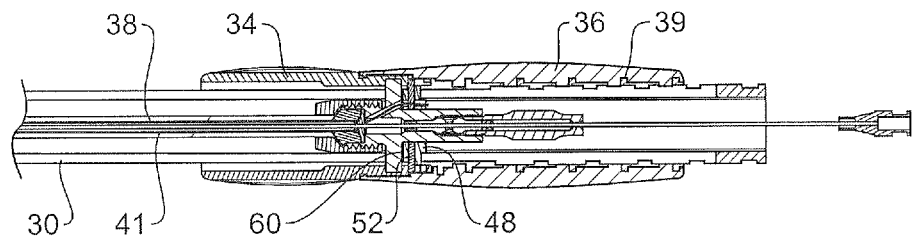

As shown in FIG. 5C continued rotation of the rotator component 36 has caused further retraction of the release handle 30 and hence also the sheath 18 with respect to the fixed handle 34 and rotator component 36 which in turn has caused the stent graft 64 to be more exposed and the stepped shoulder 60 to just engage against the release clamp 48 as discussed above. This stage is also shown in FIG. 4B. The stent graft has partially expanded under the action of its self expanding stents. The physician can at this stage review the position of the stent graft in the vasculature and make any necessary adjustments proximally distally or rotationally. For this purpose the stent graft may include radiopaque markers (not shown).

Figure 5D:
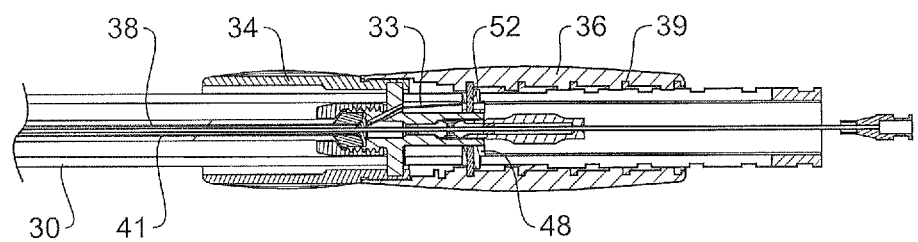

When the stent graft is correctly positioned, the rotator component 36 can then be further rotated relative to the fixed handle 34 as is shown in FIG. 5D. This will cause the release clamp 48 to move distally because the pins 52 on the release clamp are moved into engagement with the second screw thread 39 and this continues until the pins exit from the distal end of the screw thread 39. This causes the trigger wires 33 to retract from the proximal retention so that the exposed stent 66 is released and will expand as a self expanding stent and engage against the wall of the vasculature into which it is deployed.

Figure 5E:
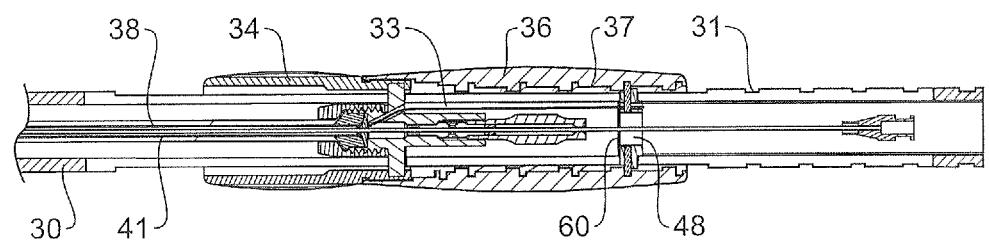

When the pins 52 disengage from the second screw thread 39 and the screw thread 31 disengages with the first screw thread 37 as shown in FIG. 5E the sheath 18 can be fully retracted off the stent graft 64 by manual distal movement of the release handle with respect to the fixed handle. At this stage the trigger wire 33 which releases the distal end of the stent graft, if present, is withdrawn from engagement with the stent graft.

The entire handle and deployment device assembly can then be withdrawn from the patient or the sheath hub 20 can be disconnected from the release handle grip 32 by separation at the bayonet connection and the sheath can be left in the patient for further operations through the sheath and the handle, pusher, guide wire catheter and nose cone dilator can be retracted through the sheath.

In essence the embodiment shown in FIGS. 1 to 5 can be characterised by the actions TTP. Twist to retract the sheath, twist to withdraw the trigger wires and pull to complete full withdrawal of the sheath.

Figure 7:
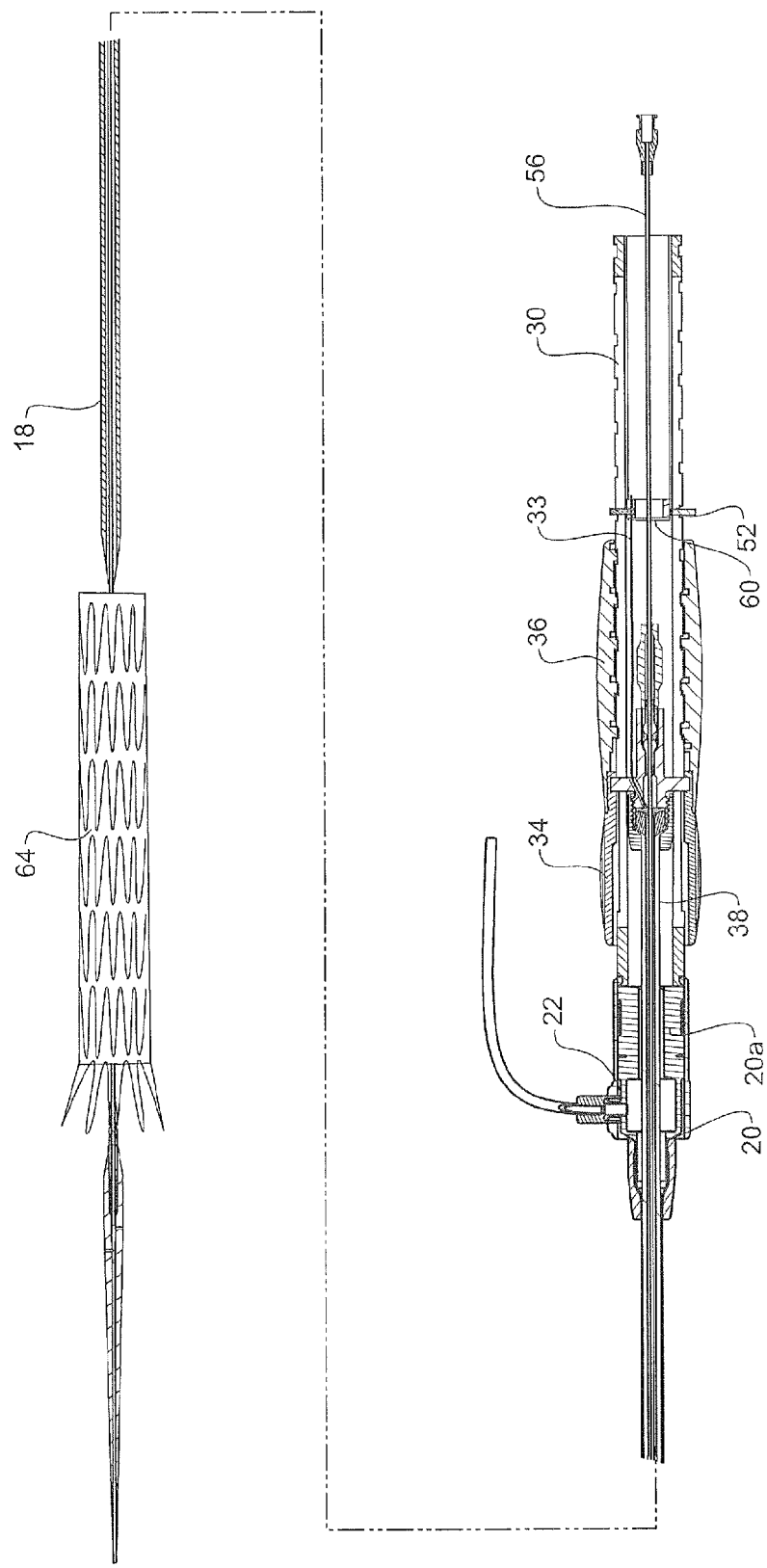
FIG. 7 shows a detailed longitudinal cross sectional view of the embodiment of FIG. 6 with the sheath fully retracted.

FIGS. 6 and 7 show an alternative embodiment of the invention. In this embodiment corresponding components to the earlier embodiment have the same reference numerals.

The handle and stent graft deployment device assembly 10 of this embodiment includes a handle portion 12 and a stent graft delivery portion 14. The delivery portion 14 is arranged to be deployed within the vasculature of a patient by the Seldinger technique to deliver and release a stent graft within the vasculature and the handle portion 12 remains outside the patient to be manipulated by a physician to deliver and release the stent graft.

The delivery portion 14 includes a nose cone dilator 16 and a sheath 18 extending from a sheath hub 20 which is engaged into the handle portion 12 with a bayonet type fitting 22. A stent graft is retained underneath the sheath 18 in the region 24 immediately distal of the nose cone dilator 16. The device is introduced into a patient over a guide wire (not shown) which passes through the guide wire catheter 56. The sheath hub 20 has haemostatic seals (not shown) through which passes the pusher 38 of the delivery device.

The handle assembly 12 comprises a release handle 30 which includes a proximal grip 32 and a fixed handle 34 to which is attached a rotator component 36. The fixed handle 34 is substantially cylindrical with a grip pattern on its outer surface. The fixed handle 34 is composed of fixed handle halves 34a and 34b which together fit around the release handle 30. The rotator component 36 is also substantially cylindrical with a grip pattern on its outer surface. The rotator component 36 has a single first screw thread on its inner surface.

In this embodiment the screw thread 31 on the outer surface of the release handle extends substantially the entire length of the release handle and engages the screw thread on the inner surface of the rotator component. Rotation of the rotator component 36 commences retraction of the sheath with respect to the pusher until the release clamp 48 is engaged with the stepped shoulder 60. At this stage both the sheath and release clam are moved distally at the same time. Continued rotation of the rotator component with respect to the fixed handle causes the sheath 18 to continue to be retracted until it is fully retracted off the stent graft 64 by distal movement of the release handle with respect to the fixed handle as shown in FIG. 7. The release clamp 48 continues to be engaged by the stepped shoulder 60 so it is carried further distally.

In essence the embodiment shown in FIGS. 6 and 7 can be characterised by the action T. Twist to retract the sheath, withdraw the trigger wires and completely withdrawal the sheath in a single smooth fluid motion. The sheath does not stop retracting whilst the proximal end of the graft is released.

FIGS. 8, 8A, 8B and 8C show a perspective view of an alternative embodiment of a deployment device according to the present invention as well as cross sectional views of specific parts of the embodiment. In this embodiment corresponding components to the earlier embodiment have the same reference numerals. It should be noted that FIG. 8B is a cross section rotated through 90 degrees to the cross section shown in FIG. 8A. In other words FIG. 8A shows a longitudinal part cross section in a vertical plane and FIG. 8B shows a longitudinal part cross section in a horizontal plane. FIG. 8C shows a perspective view of the release clamp of the embodiment shown in FIG. 8.

The handle and stent graft deployment device assembly 70 of this embodiment includes a handle portion 12 and a stent graft delivery portion 14. The delivery portion 14 is arranged to be deployed within the vasculature of a patient by the Seldinger technique to deliver and release a stent graft within the vasculature and the handle portion 12 remains outside the patient to be manipulated by a physician to deliver and release the stent graft.

The delivery portion 14 includes a nose cone dilator 16 and a sheath 18 extending from a sheath hub 20 which is engaged into the handle portion 12 with a bayonet type fitting 22. A stent graft is retained underneath the sheath 18 in the region 24 immediately distal of the nose cone dilator 16. The device is introduced into a patient over a guide wire (not shown) which passes through the guide wire catheter 56. The sheath hub 20 has haemostatic seals through which passes the pusher 38 of the delivery device.

The handle assembly 12 comprises a release handle 30 which includes a proximal grip 32 and a fixed handle 34 to which is attached a rotator component 36. The fixed handle 34 is substantially cylindrical with a grip pattern on its outer surface. The rotator component 36 is also substantially cylindrical with a grip pattern on its outer surface.

In this embodiment the screw thread 31 on the outer surface of the release handle extends substantially the entire length of the release handle so that the screw thread 31 continues to be engaged with a short screw thread 72 within the rotator component 36 as shown in FIG. 8A. Continued rotation of the rotator component 36 with respect to the fixed handle causes the sheath 18 to continue to be retracted until it is fully retracted off the stent graft 64 by distal movement of the release handle with respect to the fixed handle as shown in FIG. 7.

In this embodiment the release clamp 48 is releasably retained to the pusher hub 40 by a spring clip arrangement 73 as shown in FIG. 8B. The operation of the spring clip arrangement 73 is shown in detail in FIGS. 9A to 9D. In FIGS. 9A to 9D only part of the device is shown for clarity.

The release clamp 48 is mounted for longitudinal movement onto the cylindrical portion 50 of the pusher hub 40 but is retained immediately distal of the pusher hub by a pair of spring clips 74 which are integral with and extend distally from the pusher hub and which are received into a recess 76 in the release clamp 48 with a barb 78 on the spring clip engaging an abutment 80 on the release clamp 48.

Figure 9A:
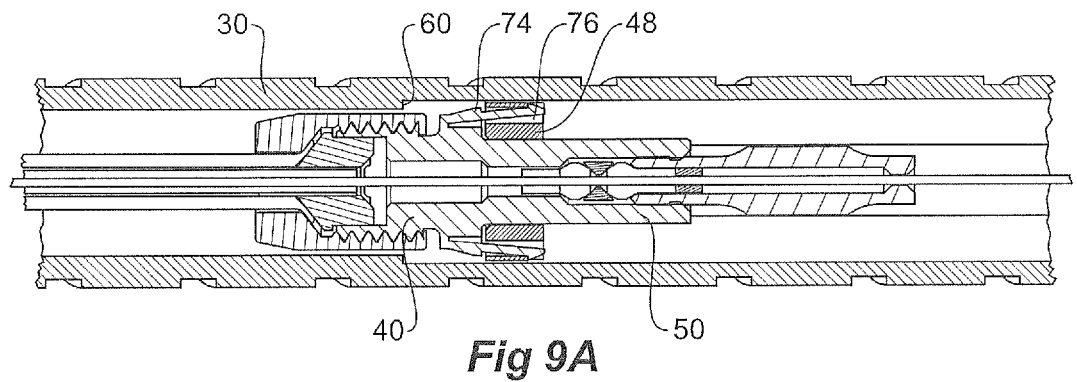
FIGS. 9A to 9D show various stages of the action of the release clamp retention system.
Figure 9B:
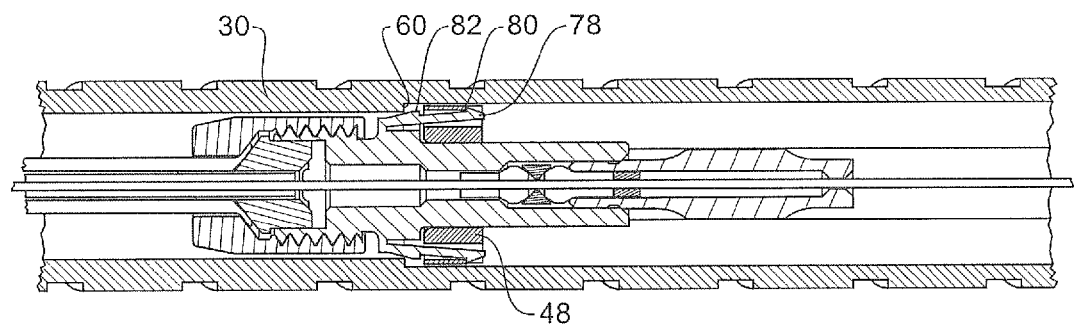
Figure 9C:
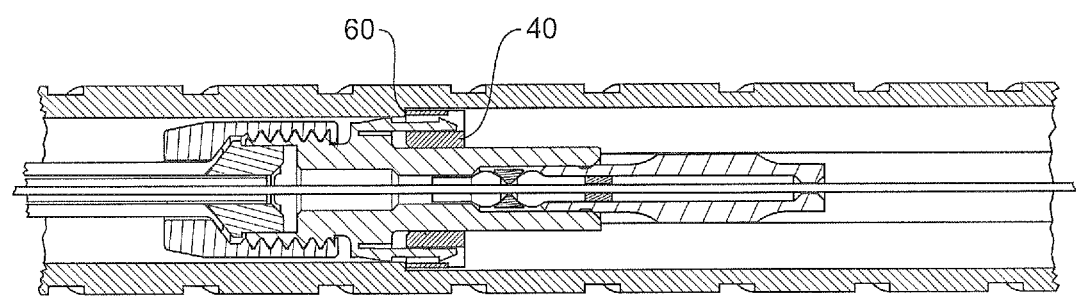
Figure 9D:
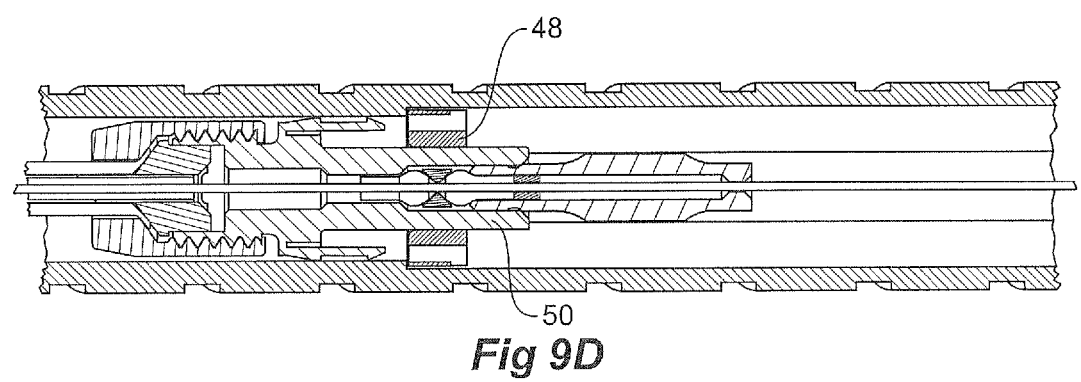

To release the release clamp from its engagement with the spring clips a shoulder 60 on the internal surface of the release handle 30 engages with the outer surface 82 of the spring clip (see FIG. 9B) which causes the barb 78 to move from its engagement with the abutment 80 (see FIG. 9C). The shoulder 60 then engages directly with the release clamp 48 and continued movement of the release handle causes distal movement of the release clamp along the cylindrical portion 50 of the pusher hub 40 (see FIG. 9C).

The shoulder 60 on the internal surface of the release handle 30 is positioned so that during the movement of the release handle with respect to the fixed handle the shoulder engages the release clamp 48 to move it distally and thereby pulls trigger wires fastened to the release clamp to release the stent graft from the delivery device 70.

FIGS. 10A to 10I show various detailed views and stages of the action of an alternative release clamp retention system. In this embodiment corresponding components to the earlier embodiment have the same reference numerals.

Figures 10A, 10B:
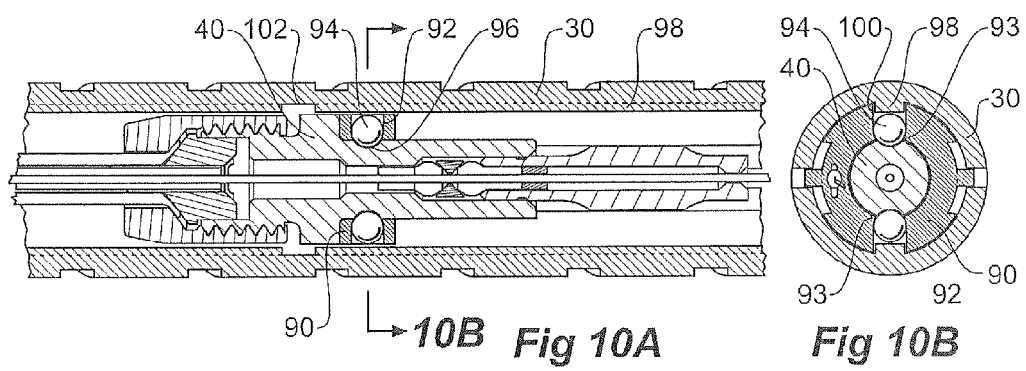
Figures 10C, 10D:
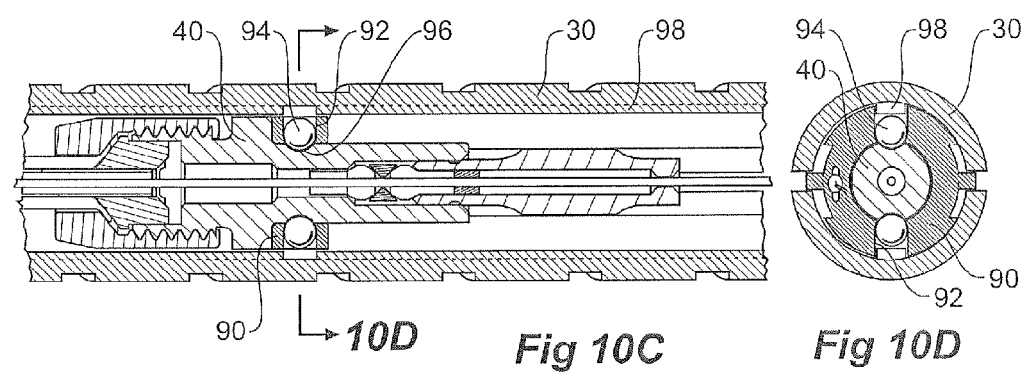
Figures 10E, 10F:
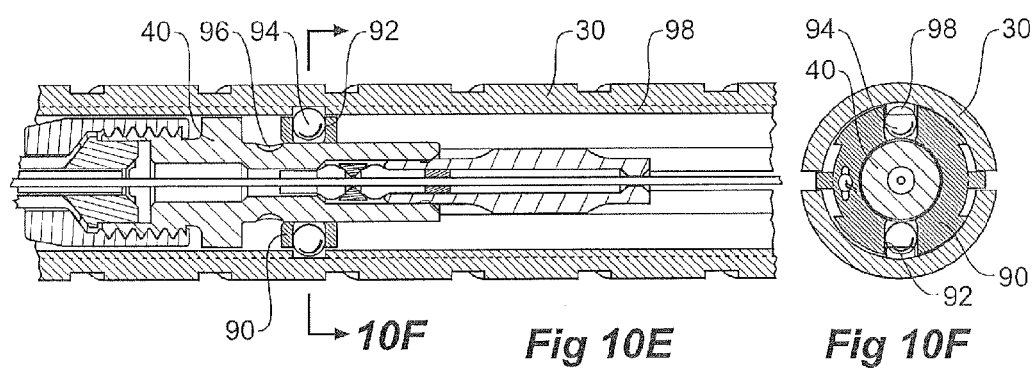

It should be noted that FIG. 10H is a cross section rotated through 90 degrees to the cross section shown in FIGS. 10A, 10C and 10E. In other words FIG. 10H shows a longitudinal part cross section in a vertical plane and FIGS. 10A, 10C and 10E show a longitudinal part cross section in a horizontal plane.

In this embodiment the release clamp 90 is retained with respect to the cylindrical portion 50 of the pusher hub 40 by a ball and detent system. The release clamp 90 has a pair of radial bores 92 into which are received balls 94. The radial bores each have an inner shoulder 93 to prevent the balls 94 from being able to pass entirely through the radial bores. In the position as shown in FIG. 10A and 10B the release clamp 90 is engaged with the cylindrical portion 50 of the pusher hub 40 by each ball 94 being received in a recess 96 in the cylindrical portion 50 of the pusher hub 40. The balls 94 are prevented from moving out of the recess 96 by a rail 98 on the inner surface of the release handle which engages into a groove 100 in the release clamp 90 and holds the ball into engagement into the recess 96 in the cylindrical portion 50 of the pusher hub 40.

As shown in FIGS. 10C and 10D when the sliding handle moves to a position where there is a recess 102 in the rail 98 the ball can move into the recess 102 and not remain engaged into the recess 96 in the cylindrical portion 50 of the pusher hub 40. Continued movement of the release handle 30 then carries the ball engaged into the recesses 102 and disengaged with the recess 96 which allows the release clamp 90 to move along the cylindrical portion 50 of the pusher hub 40 as is shown in FIGS. 10E and 10F. This causes trigger wire used for retention of parts of the stent graft as discussed above to be released. See also FIG. 10H.

FIG. 10G shows a perspective view of the release clamp. In this view it will be seen that the groove 100 and radial bores 92 are in a plane at right angles to the plane of the guide lugs 104.

FIG. 10H and 10I show a longitudinal and cross sectional view of a part of the delivery device in a plane at right angle to the views as shown in FIGS. 10A, 10C and 10E. The release clamp 90 is shown moved along the cylindrical portion 50 of the pusher hub 40. The trigger wires 30 pass through the release clamp 90 and are fastened to the rear surface at 106. As shown in FIG. 10H the trigger wires 33 have been withdrawn by movement of the release clamp 90 with respect to the pusher hub 40.

In alternative embodiments there may be screw thread portions on the proximal and distal parts of the release handle and not in the middle portion. Alternatively there may be any combination of screw threads in a portion or in whole along the length of the release handle to facilitate the required functionality.

In such an embodiment first and second screw threads are present. The first screw thread on the release handle extends proximally from the distal end of the release handle in two segments, a first thread segment from the distal end of the release handle, then a portion of no first thread, then a second thread segment of the first thread for a selected length. The second screw thread on the internal surface of the rotator component has a twin thread, one to engage the first screw thread and another to be engaged by pins on the release clamp in a manner similar to that discussed above.

The second screw thread engaging with the first screw thread moves the release handle to retract the sheath. Just prior to the first of the twin threads in rotator component disengaging from first thread segment on the release handle, the pin on the release clamp is engaged into a second of the twin threads within the rotator component by a first stepped shoulder within the release handle by use of a first thread overlap. Once the pin on the release clamp is engaged into the second thread and the first thread is disengaged (in the space portion between the first and second first thread segments) the release handle and hence the sheath remain static whilst the release clamp is pulled back with the second of the twin threads to release the trigger wires. Then just prior to the pin on the release clamp coming to the end of the second thread in the rotator, the release clamp acts on a second stepped shoulder in the release handle by use of a second thread overlap. The release clamp pushes the release handle so that the second thread segment of first thread on the release handle can engage with the first thread in the rotator. Then when the first thread in the rotator is engaged with the second thread segment on the release handle and the pin of the release clamp is disengaged from the second thread in the rotator, the release handle can continue to retract by turning of the rotator. This will also further retract the trigger wires until the distal end of the graft is released just after the sheath fully exposes the graft.

This embodiment can be referred to as a TTT version. Turn to retract sheath, turn to retract trigger wires and turn to complete retraction of sheath.

Figure 11:
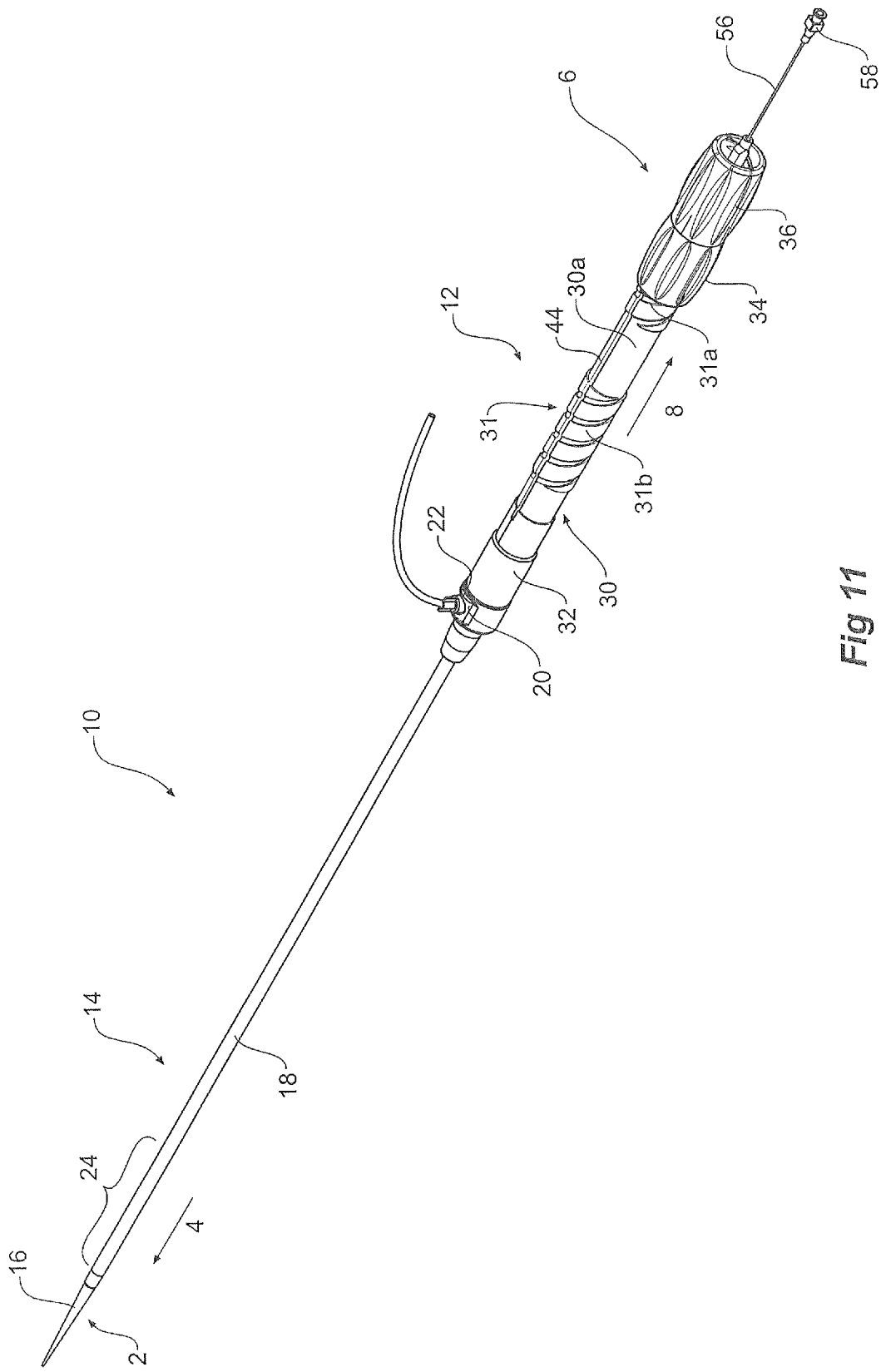
FIG. 11 shows a perspective view of an alternative embodiment of a deployment device according to the present invention.

FIG. 11 shows a perspective view of this alternative embodiment of a deployment device according to the present invention. In this embodiment corresponding components to the earlier embodiment have the same reference numerals.

The handle and stent graft deployment device assembly 10 of this embodiment includes a handle portion 12 and a stent graft delivery portion 14. The delivery portion 14 is arranged to be deployed within the vasculature of a patient by the Seldinger technique to deliver and release a stent graft within the vasculature and the handle portion 12 remains outside the patient to be manipulated by a physician to deliver and release the stent graft.

The delivery portion 14 includes a nose cone dilator 16 and a sheath 18 extending from a sheath hub 20 which is engaged into the handle portion 12 with a bayonet type fitting 22. A stent graft is retained underneath the sheath 18 in the region 24 immediately distal of the nose cone dilator 16. The device is introduced into a patient over a guide wire (not shown) which passes through the guide wire catheter 56. The sheath hub 20 has haemostatic seals (not shown) through which passes the pusher 38 of the delivery device.

The handle assembly 12 comprises a release handle 30 which includes a proximal grip 32 and a fixed handle 34 to which is attached a rotator component 36. The fixed handle 34 is substantially cylindrical with a grip pattern on its outer surface. The fixed handle 34 is composed of fixed handle halves 34a and 34b which together fit around the release handle 30. The rotator component 36 is also substantially cylindrical with a grip pattern on its outer surface. The rotator component 36 has a single first screw thread on its inner surface.

In this embodiment the screw thread 31 on the outer surface of the release handle extends in two segments. A first thread segment 31a from the distal end of the release handle, then a portion of no first thread 30a, then a second thread segment 31b of the first thread for a selected length. Otherwise the construction is the same as that discussed in relation to FIG. 6 and the operation of the device is a discussed above.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. An endovascular introducer comprising in combination, a handle assembly, a stent graft deployment device and a stent graft retained on the stent graft deployment device;
the handle assembly including a fixed handle and a release handle, the release handle to be moved relative to the fixed handle, the fixed handle comprising a fixed portion to be gripped and held by a user and a rotating portion to be rotated, the rotating portion of the fixed handle and the release handle comprising co-acting first screw threads whereby rotation of the rotating portion of the fixed handle causes relative longitudinal motion between the fixed handle and the release handle;
the deployment device including a pusher assembly, the stent graft being mounted onto the pusher assembly and a sheath to cover the stent graft on the pusher assembly and to retain the stent graft in a compressed condition on the pusher assembly, the sheath being relatively movable with respect to the pusher assembly, the pusher assembly being connected to the fixed handle and the sheath being connected to the release handle;
whereby retraction of the release handle with respect to the fixed handle by the relative rotation thereof causes the sheath to be retracted at least partially from the stent graft on the pusher assembly, wherein the fixed portion of the fixed handle engages the pusher and the rotating portion of the fixed handle engages a release clamp on the pusher, the release clamp being movable longitudinally with respect to the pusher, the release clamp on the pusher having attached thereto trigger wires for the release of the stent graft from the pusher assembly, whereby rotation of the rotating portion of the fixed handle moves the release clamp on the pusher and thereby pulls the trigger wires to release the stent graft from the pusher assembly.

2. An endovascular introducer as in claim 1, wherein the rotating portion of the fixed handle rotates with respect to the fixed portion of the fixed handle and the rotating portion includes a second screw thread with a portion of the release clamp engaged into the second screw thread whereby rotational movement of the rotating portion of the fixed handle causes longitudinal movement of the release clamp with respect to the pusher assembly.

3. An endovascular introducer as in claim 2, wherein the rotating portion comprises an internal cylindrical surface and both the first screw thread and the second screw thread are formed on the internal cylindrical surface, the first screw thread and the second screw thread comprising the same pitch and being concentric with each other.

4. An endovascular introducer as in claim 3, wherein the first screw thread comprises a 3 mm by 1 mm helical protrusion with a 32 mm pitch on the internal cylindrical surface of the rotating portion and the second screw thread comprises a 2 mm by 2 mm helical groove with a 32 mm pitch on the internal cylindrical surface of the second component.

5. An endovascular introducer as in claim 1, wherein the co-acting first screw thread on the release handle extends part of the length of the release handle.

6. An endovascular introducer as in claim 1, wherein the co-acting first screw thread on the release handle extends substantially the full length of the release handle.

7. An endovascular introducer as in claim 1, further including a stepped shoulder on the release handle, the stepped shoulder arranged to engage the release clamp on the pusher assembly after a selected amount of movement of the release handle has occurred by the movement relative to the fixed handle to thereby cause the portion of the release clamp to engage into the second screw thread to thereby start to pull the trigger wires to release of the stent graft from the pusher assembly.

8. A stent graft deployment device assembly, the device including a cylindrical fixed handle to be gripped and held by a user and a tubular release handle extending through the fixed handle whereby the release handle can be moved through the fixed handle, the deployment device assembly further including a pusher assembly and a sheath to cover a stent graft on the pusher assembly, the pusher assembly being connected to the fixed handle and the sheath being connected to the release handle whereby retraction of the release handle through the fixed handle causes the sheath to be retracted from the stent graft on the pusher assembly, the fixed handle includes a grip component which grips the pusher assembly and the rotator component, the rotator component comprising a first screw thread and a second screw thread on an internal cylindrical surface thereof, the first screw thread and the second screw thread comprising the same pitch and being concentric with the first screw thread, the tubular release handle comprising an external screw thread which is engaged with the first screw thread, a release clamp on the pusher assembly, the release clamp on the pusher assembly having trigger wires for the release of the stent graft from the pusher assembly attached thereto, the release clamp comprising pins engaging with the second screw thread whereby movement of the rotator component with respect to the grip component first moves the tubular release handle with respect to the grip component and subsequently moves the release clamp on the pusher assembly and thereby pulls the trigger wires.

9. A stent graft deployment device assembly as in claim 8 wherein the external screw thread on the tubular release handle extends part of the length of the tubular release handle from a distal end thereof.

10. A stent graft deployment device assembly as in claim 8 wherein the external screw thread on the tubular release handle extends substantially the full length of the tubular release handle from a distal end thereof.

11. A stent graft deployment device assembly as in claim 8 wherein the first screw thread comprises a 3 mm by 1 mm helical protrusion with a 32 mm pitch on the internal cylindrical surface of the rotator component and the second screw thread comprises a 2 mm by 2 mm helical groove with a 32 mm pitch on the internal cylindrical surface of the rotator component and the external screw thread which engages with the first screw thread comprises a 3 mm by 1 mm helical groove with a 32 mm pitch.

12. A stent graft deployment device assembly as in claim 8 wherein the release handle includes a bayonet socket for a hub of the sheath.

13. A stent graft deployment device assembly as in claim 12 wherein the first screw thread on the release handle extends from the distal end of the release handle in two segments, a first thread segment from the distal end of the release handle, then a portion of no first thread, then a second thread segment of the first thread for a given length and the second screw thread on the internal surface of the rotator component comprises a twin thread, one to engage the first screw thread and another to be engaged by pins on the release clamp, wherein the first screw thread moves the release handle to retract the sheath and just prior to first thread in rotator component disengaging from first thread segment on release handle, the pin on the release clamp is engaged into a second thread within the rotator component by a first stepped shoulder by use of a first thread overlap and once the pin on the release clamp is engaged into the second thread and the first thread is disengaged in the space portion between the first and second first-thread segments the release handle and hence the sheath remain static whilst the release clamp is pulled back with the second thread to release the trigger wires and subsequently the second thread segment of first thread on the release handle engages with the first thread in the rotator.

14. A stent graft deployment device assembly as in claim 8 wherein the fixed handle comprises a substantially cylindrical bore therethrough and the release handle is tubular and slides within the fixed handle.

15. A stent graft deployment device assembly as in claim 8 wherein the tubular release handle has longitudinal slots therealong and an internal lumen and the pusher assembly extends within the longitudinal lumen and the pusher assembly includes arms which extend through the longitudinal slots to engage with the fixed handle whereby the release handle can be moved with respect to the fixed handle to move the sheath with respect to the pusher assembly.

16. A stent graft deployment device assembly as in claim 8 further including a stepped shoulder on the release handle, the stepped shoulder arranged to engage the release clamp on the pusher assembly after a selected amount of movement of the release handle has occurred by the relative rotation of the rotator component to thereby pull the trigger wires to release of the stent graft from the pusher assembly.

17. A stent graft deployment device assembly as in claim 8 wherein the stepped shoulder is inside the release handle.

18. A stent graft deployment device assembly as in claim 8 wherein the release clamp on the pusher is retained on the pusher by a releasable spring clip, the second component comprising a shoulder to engage and release the releasable spring clip whereby movement longitudinally of the second component with respect to the first component causes the shoulder to engage with and release the releasable spring clip thereby moving the release clamp on the pusher and thereby pulling the trigger wires to release the stent graft from the pusher assembly.

19. A stent graft deployment device assembly as in claim 8 wherein the release clamp on the pusher is retained on the pusher by a ball and detent arrangement.

20. A stent graft deployment device assembly as in claim 19 wherein the ball and detent arrangement comprises a ball retained on the release clamp and engaged into a detent on the pusher and a recess in the second component, wherein, when movement of the second component causes the recess in the second component to be opposite to the ball, the ball is released from its engagement with the detent on the pusher and the release clamp can move with respect to the pusher.

* * * * *